US00PP09042P

United States Patent [19]

Meilland

[11] Patent Number: Plant 9,042

[45] Date of Patent: Jan. 17, 1995

[54] HYBRID TEA ROSE PLANT NAMED MEIPALEO

[75] Inventor: Alain A. Meilland, Antibes, France

[73] Assignee: The Conard-Pyle Company, West Grove, Pa.

[21] Appl. No.: 215,528

[22] Filed: Mar. 22, 1994

[51] Int. Cl.[6] ..... A01H 5/00
[52] U.S. Cl. ..... Plt./15
[58] Field of Search ..... Plt. 15, 24

*Primary Examiner*—Howard J. Locker

*Attorney, Agent, or Firm*—Burns, Doane, Swecker & Mathis

[57] ABSTRACT

A new and distinct variety of Hybrid Tea rose plant is provided which abundantly and continuously forms attractive fragrant intense yellow blossoms. Such blossoms are long lasting and exhibit good petal-drop characteristics. The plant exhibits an erect growth habit, vigorous vegetation, decorative foliage, and is well suited for use as attractive ornamentation in the landscape. Additionally, the plant exhibits good disease resistance.

1 Drawing Sheet

SUMMARY OF THE INVENTION

The new variety of Hybrid Tea rose plant was created by artificial pollination wherein two parents were crossed which previously had been studied in the hope that they would contribute the desired characteristics. The female parent (i.e., the seed parent) of the new variety was the Meinuzeten variety (U.S. Plant Pat. No. 4,224). The male parent (i.e., the pollen parent) was formed by the cross of the Sunbright variety (U.S. Plant Pat. No. 4,438) and the Anne-Lise Rothenberger variety (nonpatented in the United States). The parentage of the new variety can be summarized as follows:

MEINUZETEN×(SUNBRIGHT×ANNE-LISE ROTHENBERGER).

The seeds resulting from the above pollination were sown and 45 small plants were obtained which were physically and biologically different from each other. Selective study resulted in the identification of a single plant of the new variety.

It was found that the new variety of Hybrid Tea rose plant of the present invention possesses the following combination of characteristics:

(a) forms in abundance on a continuous basis attractive fragrant long lasting intense yellow blossoms,
(b) exhibits an erect growth habit with decorative foliage,
(c) exhibits vigorous vegetation,
(d) is particularly suited for growing in the landscape, and
(e) exhibits good disease resistance.

The new variety well meets the needs of the horticultural industry and is particularly well suited for use as attractive ornamentation in the landscape.

The new variety has been found to undergo asexual propagation in France by a number of routes, including budding, grafting, and cuttage. The characteristics of the new variety have been found to be stable and are strictly transmissible by such asexual propagation from one generation to another.

The new variety has been named the Meipaleo variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were two years of age and wer observed during June while budded on *Rosa froebelii* understock and growing outdoors at Le Cannet des Maures, Var, France.

FIG. 1—illustrates a specimen of a young shoot;

FIG. 2—illustrates a specimen of a floral bud before the opening of the sepals;

FIG. 3—illustrates a specimen of a floral bud at the opening of the sepals;

FIG. 4–illustrates a specimen of a floral bud at the opening of the petals;

FIG. 5—illustrates a specimen of a flower in the course of opening;

FIG. 6—illustrates a specimen of a fully open flower — plan view — obverse;

FIG. 7—illustrates a specimen of a fully open flower — plan view — reverse;

FIG. 8—illustrates a specimen of a fully open flower prior to petal drop — plan view — obverse;

FIG. 9—illustrates a specimen of a fully open flower prior to petal drop — plan view — reverse;

FIG. 10—illustrates a specimen of a floral receptacle showing the arrangement of the stamens and pistils;

FIG. 11—illustrates a specimens of a floral receptacle showing the arrangement of the pistils (stamens removed);

FIG. 12—illustrates a specimen of a flowering stem;

FIG. 13—illustrates a specimen of a main branch;

FIG. 14—illustrates a specimen of a leaf with three leaflets — plan view — under surface;

FIG. 15—illustrates specimens of two leaves with five leaflets — plan view — with the under surface being shown on the left and the upper surface being shown on the right; and FIG. 16—illustrates a specimen of a leaf with seven leaflets — plan view — upper surface.

DETAILED DESCRIPTION

Figures 1, 2, 3, 4, 5, 6, 7, 8, 9, 10, 11, 12, 13, 14, 15, 16:
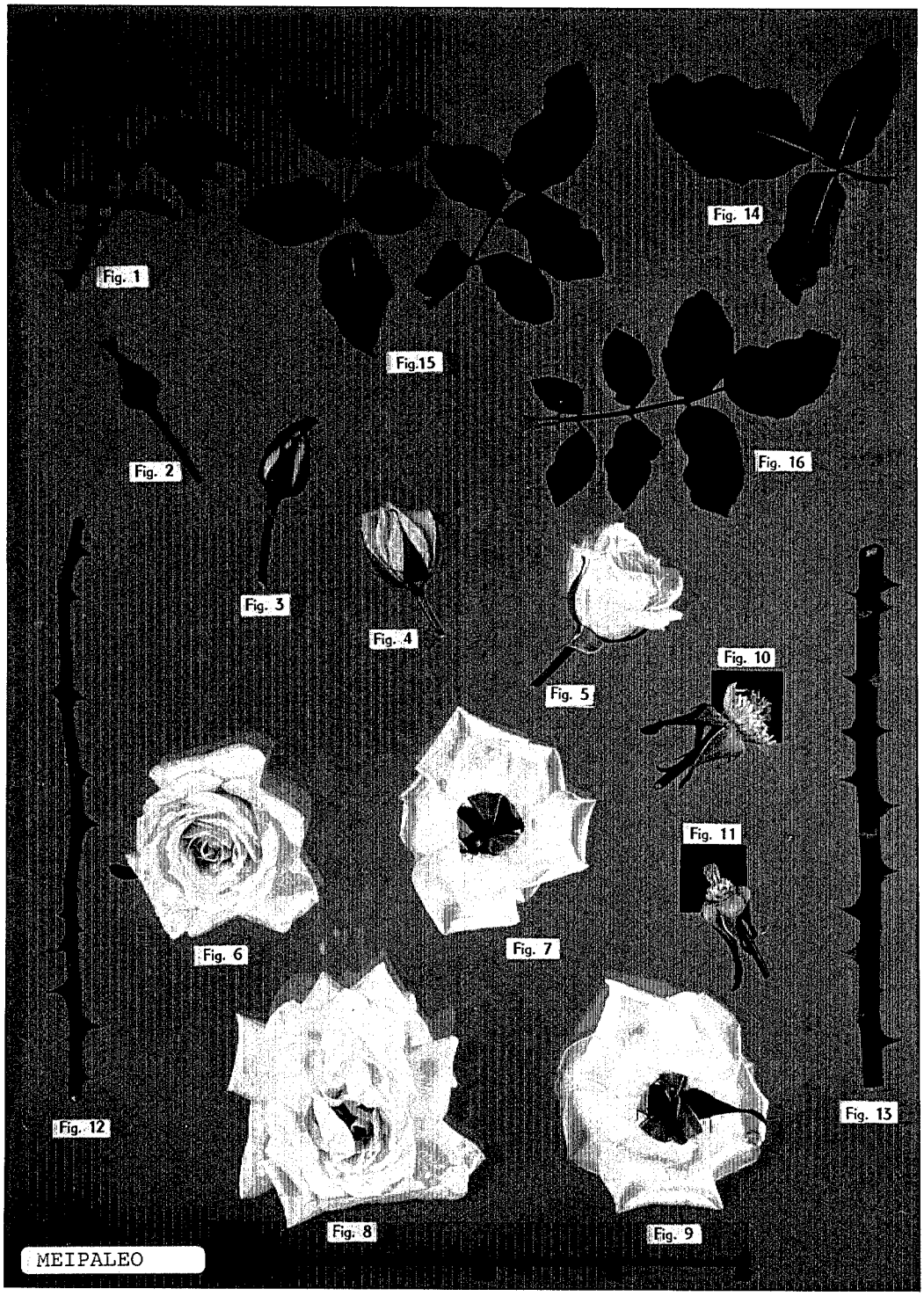

The chart used in the identification of the colors is that of The Royal Horticultural Society (R.H.S. Colour Chart). The description is based on the observation of three year-old plants while budded on *Rosa froebelii* understock and growing outdoors at Le Cannet des Maures, Var, France. The coloration in common terms precedes reference to the chart.

Class: Hybrid Tea.

Plant:

*Height.*—Approximately 80 to 90 cm. on average at the end of the growing season.

*Habit.*—Erect.

Branches:

*Color.*—Young stems: medium green, Yellow-Green Group 146B, suffused with some reddish coloration. Adult wood: bronze green, Yellow-Green Group 146A.

*Thorns.*—Size: medium. Quantity: numerous. Color: reddish on young stems and pinkish on mature wood.

Leaves:

*Stipules.*—Adnate, pectinate, large, and linear.

*Petioles.*—Upper surface: striped reddish brown on young foliage and medium green on adult foliage with more or less glandular edges. Under syrface: light green without prickles.

*Leaflets.*—Number: 3, 5 (most often), and 7. Shape: elliptic. Serration: single and regular. Texture: leathery. General appearance: dense, medium green, and semi-glossy. Color (young foliage): upper surface: medium green, Yellow-Green Group 146B, and more or less suffused with reddish-brown coloration. under surface: light green, Yellow-Green Group 146C, and more or less stained with reddish-brown coloration. Color (adult foliage): upper surface: medium green, Green Group 137A. under surface: light green, Green Group 137C.

Inflorescence:

*Number of flowers.*—Generally one to three per stem.

*Peduncle.*—Light green, smooth, and more or less toned with reddish coloration. The length is approximately 4.5 cm. on average.

*Sepals.*—Upper surface: tomentose, greenish, and more or less stained with reddish coloration. Under surface: light green with more or less glandular edges.

*Buds.*—Shape: conical. Length: approximately 3 cm. on average. Size: large. Color upon opening: upper surface: Buttercup Yellow, Yellow-Orange Group 15A. under surface: Lemon Yellow, Yellow Group 13B.

*Flower.*—Shape: cuplike with parallel sides. Diameter: approximately 11 cm. on average. Color (when opening begins): upper surface: Lemon Yellow, Yellow Group 12A, and suffused with Chrome Yellow, Yellow-Orange Group 15C. under surface: light Lemon Yellow, Yellow Group 13C. Color (when blooming): upper surface: Lemon Yellow, Yellow Group 12A, and commonly lighter at the edges. under surface: Lemon Yellow, Yellow Group 12B, and commonly lighter at the edges. Color (at end of opening): upper surface: Lemon Yellow, Yellow Group 12B, and commonly lighter at the edges. under surface: Lemon Yellow, Yellow Group 12C, and commonly lighter at the edges. Fragrance: medium. Lasting quality: long. Petal number: approximately 35 on average. Petal shape: rounded with reflexed edges. Petal drop: good. Stamen number: approximately 122 on average. Anthers: Normal ochre in coloration. Filaments: yellow in coloration, and commonly of irregular heights. Pistils: approximately 92 on average. Stigmas: normal. Styles: very tomentose near the base. Receptacle: medium green and sometimes toned with reddish coloration, and in longitudinal section at the dehiscence of the anthers it is in the shape of a large funnel.

Development:

*Vegetation.*—Strong and vigorous.

*Blooming.*—Abundant and continuous.

*Aptitude to bear fruits.*—Good.

*Resistance to frost.*—Good.

*Resistance to diseases.*—Very good.

I claim:

1. A new and distinct variety of Hybrid Tea rose plant characterized by the following combination of characteristics:

(a) forms in abundance on a continuous basis attractive fragrant long lasting intense yellow blossoms,
(b) exhibits an erect growth habit with decorative foliage,
(c) exhibits vigorous vegetation,
(d) is particularly suited for growing in the landscape, and
(e) exhibits good disease resistance;

substantially as herein shown and described.

* * * * *

MEIPALEO